United States Patent
Matsuzaki

(10) Patent No.: US 9,232,798 B2
(45) Date of Patent: Jan. 12, 2016

(54) PESTICIDAL COMPOSITION AND ITS USE

(75) Inventor: Yuichi Matsuzaki, Toyonaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 253 days.

(21) Appl. No.: 13/643,837

(22) PCT Filed: Apr. 25, 2011

(86) PCT No.: PCT/JP2011/002423
§ 371 (c)(1),
(2), (4) Date: Jan. 4, 2013

(87) PCT Pub. No.: WO2011/135840
PCT Pub. Date: Nov. 3, 2011

(65) Prior Publication Data
US 2013/0116294 A1    May 9, 2013

(30) Foreign Application Priority Data
Apr. 27, 2010    (JP) ................. 2010-101845

(51) Int. Cl.
*A01N 43/56*    (2006.01)

(52) U.S. Cl.
CPC ...................... *A01N 43/56* (2013.01)

(58) Field of Classification Search
CPC .... A01N 43/56; A01N 47/02; A01N 2300/00
See application file for complete search history.

(56) References Cited

U.S. PATENT DOCUMENTS

| | | |
|---|---|---|
| 4,536,506 A | 8/1985 | Marcoux et al. |
| 4,742,074 A * | 5/1988 | Nishida et al. ............... 514/406 |
| 5,093,347 A | 3/1992 | Graneto et al. |
| 5,948,819 A | 9/1999 | Ohtsuka et al. |
| 7,232,836 B2 | 6/2007 | Lahm et al. |
| 7,612,100 B2 | 11/2009 | Koyanagi et al. |
| 7,902,231 B2 | 3/2011 | Lahm et al. |
| 7,994,201 B2 | 8/2011 | Koyanagi et al. |
| 8,148,521 B2 | 4/2012 | Lahm et al. |
| 8,158,802 B2 | 4/2012 | Lahm et al. |
| 2002/0019541 A1 | 2/2002 | Eberle et al. |
| 2004/0214828 A1 | 10/2004 | Selby |
| 2005/0222051 A1 | 10/2005 | Andersch et al. |
| 2007/0004921 A1 | 1/2007 | Dunkel et al. |
| 2007/0244121 A1 | 10/2007 | Walter et al. |
| 2007/0265267 A1 | 11/2007 | Walter et al. |
| 2008/0070785 A1 | 3/2008 | Walter et al. |
| 2009/0104145 A1 | 4/2009 | Hughes et al. |
| 2009/0123561 A1 | 5/2009 | Gewehr et al. |
| 2009/0181956 A1 | 7/2009 | Ikegami et al. |
| 2009/0247511 A1 | 10/2009 | Suty-Heinze et al. |
| 2009/0286681 A1 | 11/2009 | Dahmen et al. |
| 2009/0320166 A1 | 12/2009 | Suty-Heinze et al. |
| 2010/0029698 A1 | 2/2010 | Voeste et al. |
| 2010/0056594 A1 | 3/2010 | Sakurai et al. |
| 2010/0099559 A1 | 4/2010 | Dietz et al. |
| 2010/0120866 A1 | 5/2010 | Nokura et al. |
| 2010/0216640 A1 | 8/2010 | Tobler et al. |
| 2011/0098176 A1 | 4/2011 | Gewehr et al. |
| 2011/0105321 A1 | 5/2011 | Breuninger et al. |
| 2011/0105579 A1 | 5/2011 | Wilhelm et al. |
| 2011/0257231 A1 | 10/2011 | Koyanagi et al. |
| 2011/0319262 A1 | 12/2011 | Schade et al. |
| 2012/0171183 A1 | 7/2012 | Lahm et al. |
| 2014/0141972 A1 | 5/2014 | Berger et al. |

FOREIGN PATENT DOCUMENTS

| | | |
|---|---|---|
| EA | 011551 B1 | 4/2009 |
| EA | 011585 B1 | 4/2009 |
| EP | 2100505 A1 | 9/2009 |
| JP | 62-96472 A | 5/1987 |
| JP | 3729825 B2 | 12/2005 |
| JP | 2006-213665 A | 8/2006 |
| JP | 2008-509189 A | 3/2008 |
| JP | 2008-515834 A | 5/2008 |

(Continued)

OTHER PUBLICATIONS

International Search Report for International Patent Application No. PCT/JP2011/002423, dated Jul. 19, 2011.
Extended European Search Report for European Application No. 11774626.3, dated Oct. 31, 2013.
Oda et al., "Quantitative Structure-Activity Relationships of 2-Chloropyridine-3-carboxamide Fungicides," J. Pesticide Sci., vol. 18, No. 1, 1993, XP009026800, pp. 49-57.
DELP, "Coping with Resistance to Plant Disease," Plant Disease, vol. 64, No. 7, Jul. 1980, pp. 652-657.
International Search Report for International Patent Application No. PCT/JP2011/002410, dated Jun. 28, 2011.
International Search Report for International Patent Application No. PCT/JP2011/002411, dated Jul. 5, 2011.

(Continued)

*Primary Examiner* — Sarah Pihonak
*Assistant Examiner* — Jason A Deck
(74) *Attorney, Agent, or Firm* — Birch, Stewart, Kolasch & Birch, LLP

(57) ABSTRACT

A composition comprising a carboxamide compound represented by following formula (I), wherein $R^1$ represents a hydrogen atom or a methyl group, and $R^2$ represents a methyl group, a difluoromethyl group or a trifluoromethyl group, and one or more phenylpyrazole compounds selected from group (A) consisting of fipronil and ethiprole is provided by the present invention, and this composition has an excellent pesticidal effect.

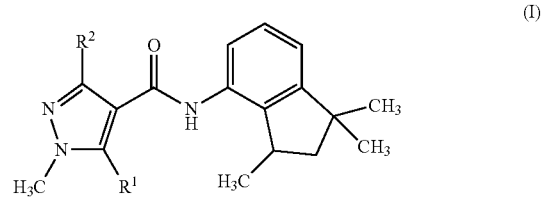

(I)

5 Claims, No Drawings

(56) References Cited

FOREIGN PATENT DOCUMENTS

| | | |
|---|---|---|
| JP | 4150379 B2 | 9/2008 |
| JP | 2008-280335 A | 11/2008 |
| JP | 2009-502747 A | 1/2009 |
| JP | 2009-502827 A | 1/2009 |
| JP | 2010-13389 A | 1/2010 |
| JP | 2010-83869 A | 4/2010 |
| JP | 2010-83883 A | 4/2010 |
| RU | 2003 125 855 A | 1/2005 |
| RU | 2264388 C2 | 11/2005 |
| RU | 2 292 138 C2 | 1/2007 |
| RU | 2298007 C2 | 4/2007 |
| WO | WO 86/02841 A1 | 5/1986 |
| WO | WO 92/12970 A1 | 8/1992 |
| WO | WO 95/27693 A1 | 10/1995 |
| WO | WO 02/059086 A1 | 8/2002 |
| WO | WO 2004/067528 A1 | 8/2004 |
| WO | WO 2005/077934 A1 | 8/2005 |
| WO | 2007-182422 A | 7/2007 |
| WO | WO 2007/095229 A2 | 8/2007 |
| WO | WO 2007/108483 A1 | 9/2007 |
| WO | WO 2008/046533 A2 | 4/2008 |
| WO | WO 2008/095913 A2 | 8/2008 |
| WO | WO 2008/113654 A2 | 9/2008 |
| WO | WO 2008/126933 A2 | 10/2008 |
| WO | WO 2008/131901 A1 | 11/2008 |
| WO | WO 2009/062905 A1 | 5/2009 |
| WO | WO 2009/098223 A2 | 8/2009 |
| WO | WO 2009098225 A2 * | 8/2009 |
| WO | WO 2009/119872 A2 | 10/2009 |
| WO | WO 2010/000790 A1 | 1/2010 |
| WO | WO 2010/021404 A2 | 2/2010 |
| WO | WO 2010/024365 A1 | 3/2010 |
| WO | WO 2010/024422 A1 | 3/2010 |
| WO | WO 2010/040623 A1 | 4/2010 |

OTHER PUBLICATIONS

International Search Report for International Patent Application No. PCT/JP2011/002413, dated Jul. 19, 2011.
International Search Report for International Patent Application No. PCT/JP2011/002414, dated Jul. 12, 2011.
International Search Report for International Patent Application No. PCT/JP2011/002415, dated Jul. 19, 2011.
International Search Report for International Patent Application No. PCT/JP2011/002416, dated May 31, 2011.
International Search Report for International Patent Application No. PCT/JP2011/002417, dated Jul. 26, 2011.
International Search Report for International Patent Application No. PCT/JP2011/002418, dated May 31, 2011.
International Search Report for International Patent Application No. PCT/JP2011/002419, dated May 31, 2011.
International Search Report for International Patent Application No. PCT/JP2011/002420, dated May 31, 2011.
International Search Report for International Patent Application No. PCT/JP2011/002421, dated May 31, 2011.
International Search Report for International Patent Application No. PCT/JP2011/002422, dated May 31, 2011.
Office Action for U.S. Appl. No. 13/643,576, dated Jun. 12, 2013.
Office Action for U.S. Appl. No. 13/643,577, dated Jun. 11, 2013.
Office Action for U.S. Appl. No. 13/643,818, dated Aug. 20, 2013.
Office Action for U.S. Appl. No. 13/643,846, dated Aug. 7, 2013.
Office Action for U.S. Appl. No. 13/643,913, dated Apr. 26, 2013.
Office Action for U.S. Appl. No. 13/643,960, dated Aug. 1, 2013.
Japanese Office Action dated Jan. 13, 2015, for Japanese Application No. 2011-097979 with the English translation.
Japanese Office Action dated Jan. 27, 2015, for Japanese Application No. 2011-099111 with the English translation.
Japanese Office Action dated Jan. 27, 2015, for Japanese Application No. 2011-099112 with the English translation.
Japanese Office Action dated Jan. 6, 2015, for Japanese Application No. 2011-096842 with the English translation.
Japanese Office Action dated Jan. 6, 2015, for Japanese Application No. 2011-096843 with the English translation.
Japanese Office Action dated Jan. 6, 2015, for Japanese Application No. 2011-097978 with the English translation.
The Decision of Grant (including an English translation), dated Apr. 10, 2015, issued in the corresponding Russian Patent Application No. 2012150829.
The Decision of Grant (including an English translation), dated Apr. 15, 2015, issued in the corresponding Russian Patent Application No. 2012150802.
The Office Action (including an English translation) issued in the corresponding Chilean Patent Application No. 2012-002988 on Apr. 24, 2015.
The Office Action issued in the corresponding Chilean Patent Application No. 2012-002976 on May 22, 2015.
The Office Action issued in the corresponding Chilean Patent Application No. 2012-002990 on May 15, 2015.
An English translation of the Chilean Office Action issued in the corresponding Chilean Patent Application No. 2012-002976 on May 22, 2015.
Chilean Application CL2011/00761, filed Apr. 6, 2011, along with an English abstract.
English translation of Chilean Office Action, issued May 15, 2015, for Chilean Application No. 2012-002990.
Russian Decision on Grant, issued Jul. 2, 2015, for Russian Application No. 2012150502, along with an English translation.
Russian Decision on Grant, issued Jun. 29, 2015, for Russian Application No. 2012150804, along with an English translation.
Russian Decision on Grant, issued May 29, 2015, for Russian Application No. 2012150436, along with an English translation.

* cited by examiner

PESTICIDAL COMPOSITION AND ITS USE

TECHNICAL FIELD

The present invention relates to a pesticidal composition and its use.

BACKGROUND ART

Many compounds have been developed for controlling pests and actually used (see, for example, PTL 1 and PTL 2).

CITATION LIST

Patent Literature

[PTL 1]: WO86/02641
[PTL 2]: WO92/12970

SUMMARY OF INVENTION

Technical Problem

An object of the present invention is to provide a composition having an excellent pesticidal effect.

Solution to Problem

The inventor of the present invention studied for seeking a composition having an excellent pesticidal effect and found that a composition comprising a carboxamide compound represented by following formula (I) and one or more phenylpyrazole compounds selected from following group (A) has an excellent pesticidal effect and then completed the present invention.

The present invention provides the following [1] to [7].

[1] A pesticidal composition comprising a carboxamide compound represented by formula (I):

[Chem. 1]

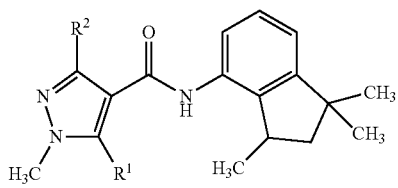

(I)

wherein
$R^1$ represents a hydrogen atom or a methyl group, and
$R^2$ represents a methyl group, a difluoromethyl group or a trifluoromethyl group,
and one or more phenylpyrazole compounds selected from group (A) consisting of fipronil and ethiprole.

[2] The pesticidal composition according to above [1], wherein the weight ratio of the carboxamide compound to the phenylpyrazole compound(s) is from 0.01/1 to 4/1 of the carboxamide compound/the phenylpyrazole compound(s).

[3] The pesticidal composition according to above [1] or [2], wherein the phenylpyrazole compound is fipronil.

[4] A method of controlling pest which comprises a step of treating a plant or the soil where a plant grows with an effective amount of a carboxamide compound represented by formula (I):

[Chem. 2]

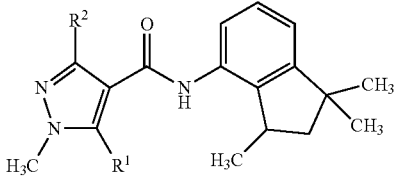

(I)

wherein
$R^1$ represents a hydrogen atom or a methyl group, and
$R^2$ represents a methyl group, a difluoromethyl group or a trifluoromethyl group, and one or more phenylpyrazole compounds selected from group (A) consisting of fipronil and ethiprole.

[5] The method of controlling pest according to above [4], wherein the weight ratio of the carboxamide compound to the phenylpyrazole compound(s) is from 0.01/1 to 4/1 of the carboxamide compound/the phenylpyrazole compound(s).

[6] The method of controlling pest according to above [4] or [5], wherein the phenylpyrazole compound is fipronil.

[7] The method of controlling pest according to any one of above [4] to [6], wherein the plant or the soil where a plant grows is soybean or the soil where soybean grows, respectively.

Advantageous Effect of Invention

According to the present invention, various pests can be controlled.

DESCRIPTION OF EMBODIMENTS

The pesticidal composition of the present invention (hereinafter referred to as "composition") comprises a carboxamide compound represented by formula (I):

[Chem. 3]

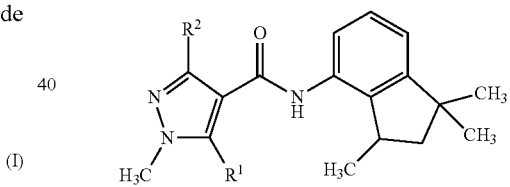

(I)

wherein
$R^1$ and $R^2$ represent the same meanings as defined in the above (hereinafter referred to as "carboxamide compound"), and one or more phenylpyrazole compounds selected from group (A) consisting of fipronil and ethiprole (hereinafter referred to as "phenylpyrazole compound").

The "carboxamide compounds" are those as described in, for example, WO86/02641 or WO92/12970, and can be prepared by the method described therein.

Particular examples of the "carboxamide compound" are as follows:
carboxamide compound represented by formula (1):

[Chem. 4]

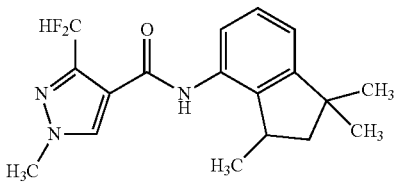

(1)

(hereinafter referred to as "carboxamide compound (1)");
carboxamide compound represented by formula (2):

[Chem. 5]

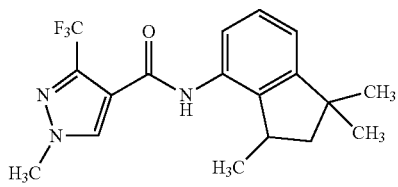

(2)

(hereinafter referred to as "carboxamide compound (2)");
carboxamide compound represented by formula (3):

[Chem. 6]

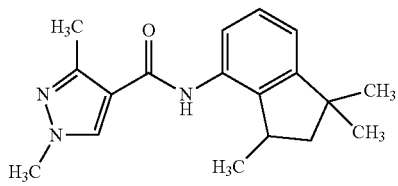

(3)

(hereinafter referred to as "carboxamide compound (3)"):
carboxamide compound represented by formula (4):

[Chem. 7]

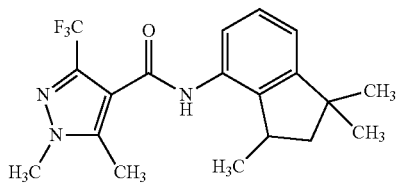

(4)

(hereinafter referred to as "carboxamide compound (4)");
carboxamide compound represented by formula (5):

[Chem. 8]

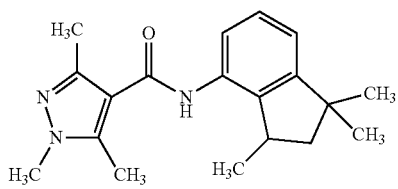

(5)

(hereinafter referred to as "carboxamide compound (5)").

The "phenylpyrazole compounds" are known compounds and described in, for example, "THE PESTICIDE MANUAL—14th EDITION (published by BCPC) ISBN 1901396142. These compounds can be obtained from the products containing said "phenylpyrazole compound" in the market or can be synthesized by publicly known methods.

The weight ratio of the "carboxamide compound" to the "phenylpyrazole compound(s)" in the "composition" is usually from 0.01/1 to 500/1, and preferably from 0.01/1 to 4/1 of "carboxamide compound"/"phenylpyrazole compound(s)"

Although the "composition" may be a mixture itself of a "carboxamide compound" and "phenylpyrazole compound(s)", the "composition" is usually prepared by mixing a "carboxamide compound", "phenylpyrazole compound(s)" and an inert carrier, and if necessary, by adding a surfactant and/or another auxiliary for formulation and by formulating the mixture into oil formulation, emulsifiable concentrate, flowable formulation, wettable powder, water dispersible granules, powder, granules, or the like. The formulation, which is used alone or by adding another inert component, can be used as a pesticide.

The total content of a "carboxamide compound" and "phenylpyrazole compound(s)" in a "composition" is usually from 0.1 to 99% by weight, preferably from 0.2 to 90% by weight, and more preferably from 1 to 80% by weight.

Examples of the solid carriers used for the formulation include fine powder or granules of, for example, mineral materials such as kaolin clay, attapulgite, bentonite, montmorillonite, acid clay, pyrophillite, talc, diatomaceous earth and calcite; natural organic materials such as corncob powder and walnut powder; synthesized organic materials such as urea; salts such as potassium carbonate and ammonium sulfate; synthetic inorganic materials such as synthesized hydrous silicon oxide. Examples of the liquid carriers include aromatic hydrocarbons such as xylene, alkylbenzene and methylnaphthalene; alcohols such as 2-propanol, ethylene glycol, propylene glycol and ethylene glycol mono-ethyl ether; ketones such as acetone, cyclohexanone and isophorone; vegetable oils such as soybean oil and cotton seed oil; petrolic aliphatic hydrocarbons; esters; dimethylsulfoxide; acetonitrile; and water. Examples of the surfactants include anionic surfactants such as alkyl sulfate ester salts, alkylarylsulfonate salts, dialkylsulfosuccinate salts, polyoxyethylene alkylaryl ether phosphoric acid ester salts, lignin sulfonate and naphthalene sulfonate formaldehyde polycondensed products; non-ionic surfactants such as polyoxyethylene alkyl aryl ethers, polyoxyethylene alkyl polyoxypropylene block copolymers and sorbitan fatty acid esters; and cationic surfactants such as alkyl trimethyl ammonium salts. Examples of the other auxiliaries for formulation include water-soluble polymers such as polyvinyl alcohol and polyvinylpyrrolidone; polysaccharides such as gum arabic, alginic acid and its salt, CMC (carboxymethylcellulose) and xanthan gum; inorganic materials such as aluminum magnesium silicate and alumina sol; preservatives; coloring agents; and stabilizers such as PAP (acidic isopropyl phosphate) and BHT.

The "composition" can be also prepared by formulating a "carboxamide compound" and "phenylpyrazole compound(s)" according to the method as described in the above, and then making the formulations or their diluents.

The "composition" can be used for protecting plants from damage by pest (for example, arthropod pest such as insect pest and acarine pest, nematode pests such as Nematoda, as well as plant disease) which gives damage to the plant by feeding, sucking, or the like.

Examples of arthropod pest and nematode pests which can be controlled by the "composition" include the followings.

Hemiptera: Planthoppers (Delphacidae) such as small brown planthopper (*Laodelphax striatellus*), brown rice planthopper (*Nilaparvata lugens*) and white-backed rice planthopper (*Sogatella furcifera*); leafhoppers (Deltocephalidae) such as green rice leafhopper (*Nephotettix cincticeps*), green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*) and brown marmorated stink bug (*Halyomorpha mista*), tarnished plant bug (*Lygus lineolaris*); whiteflies (Aleyrodidae) such as greenhouse whitefly (*Trialeurodes vaporariorum*), silverleaf whitefly (*Bemisia argentifolii*); scales (Coccidae) such as Calforina red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*); Tingidae family; Psyllidae family; and the like.

Lepidoptera: Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogate*), Indian meal moth (*Plodia interpunctella*), oriental corn borer (*Ostrinia furnacalis*), cabbage webworm (*Hellula undalis*) and bluegrass webworm (*Pediasia teterrellus*); owlet moths (Noctuidae) such as common cutworm (*Spodoptera litura*), beet armyworm (*Spodoptera exigua*), armyworm (*Pseudaletia separate*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes honmai*.), oriental tea tortrix (*Homona magnanima*), apple tortrix (*Archips fuscocupreanus*) and codling moth (*Cydia pomonella*); leafblotch miners (Gracillariidae) such as tea leafroller (*Caloptilia theivora*) and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback moth (*Plutella xylostella*); gelechiid moths (Gelechiidae) such as pink bollworm (*Pectinophora gossypiella*) and potato tuberworm (*Phthorimaea operculella*); tiger moths and allies (Arctiidae) such as fall webworm (*Hyphantria cunea*); tineid moths (Tineidae) such as casemaking clothes moth (*Tinea translucens*) and webbing clothes moth (*Tineola bisselliella*); and the like, Thysanoptera: Thrips (Thripidae) such as western flower thrips (*Frankliniella occidentalis*), melon thrips (*Thrips parmi*), yellow tea thrips (*Scirtothrips dorsalis*), onion thrips (*Thrips tabaci*), flower thrips (*Frankliniella intonsa*), tobacco thrips (*Frankliniella fusca*);

Diptera: housefly (*Musca domestica*), common mosquito (*Culex pipiens* pallens), *Tabanus* (*Tabanus trigonus*), onion fly (*Hylemya antiqua*), seed-corn fly (*Hylemya platura*), Chinese *anopheles* (*Anopheles sinensis*), Japanese leaf miner (*Agromyza oryzae*), rice leafminer (*Hydrellia griseola*), rice stem maggot (*Chlorops oryzae*), melon fly (*Dacus cucurbitae*), mediterranean fruit fly (*Ceratitis capitata*) and *Liriomyza tritrifolii*;

Coleoptera: 28-spotted ladybird (*Epilachna vigintioctopunctata*), cucurbit leaf beetle (*Aulacophora femoralis*), *Phyllotreta striolata*, rice leaf beetle (*Oulema oryzae*), rice plant weevil (*Echinocnemus squameus*), rice water weevil (*Lissorhoptrus oryzophilus*), boll weevil (*Anthonomus grandis*), adzuki bean weevil (*Callosobruchus chinensis*), zoysia billbug (*Sphenophorus venatus*), Japanese beetle (*Popillia japonica*), cupreous chafer (*Anomala cuprea*), corn rootworm families (*Diabrotica* spp.), Colorado potato beetle (*Letinotarsa decemlineata*), beetle of family Elateridae (*Agriotes* spp.), tobacco beetle (*Lasioderma serricorne*), *Anthrenus* (*Anthrenus verbasci*), rust-red flour beetle (*Tribolium castaneum*), power post beetle (*Lyctus brunneus*), whitespotted longicorn beetle (*Anoplophora malasiaca*), common pine shoot beetle (*Tomicus piniperda*), and the like;

Orthoptera: grasshoppers (*Locusta migratoria*), mole cricket (*Gryllotalpa Africana*), *Oxya yezoensis*, *Oxya japonica*, and the like;

Hymenoptera: turnip sawfly (*Athalia rosae*), leafcutter ant (*Acromyrmex* spp.), fire ants (*Solenopsis* spp.), and the like;

Blattaria: German cockroach (*Blattella germanica*), smoky-brown cockroach (*Periplaneta fuliginosa*), American cockroach (*Periplaneta americana*), black Mississippi cockroach (*Periplaneta brunnea*), Oriental cockroach (*Blatta orientalis*); Acarina: Tetranychidae such as twospotted spider mite (*Tetranychus urticae*), citrus red mite (*Panonychus citri*) and *Oligonychus* spp., Eriophyidae such as *Aculops pelekassi*, Tarsonemidae such as *Polyphagotarsonemus latus*; Tenuipalpidae; Tuckerellidae; Acaridae such as *Tyrophagus putrescentiae*, Epidermoptidae such as *Dermatophagoides farinae*, *Dermatophagoides ptrenyssnus*, Cheyletidae such as *Cheyletus eruditus*, *Cheyletus malaccensis*, *Cheyletus moorei*, and the like.

Nematoda: *Pratylenchus coffeae*, *Pratylenchus fallax*, *Heterodera glycines*, *Globodera rostochiensis*, *Meloidogyne hapla*, *Meloidogyne incognita*, *Aphelenchoides besseyi*, *Nothotylenchus acris*, and the like.

Examples of the plant diseases which can be controlled by the "composition" include the followings.

Rice diseases: *Magnaporthe grisea*, *Cochliobolus miyabeanus*, *Rhizoctonia solani*, *Gibberella fujikuroi*;

Wheat diseases: *Erysiphe graminis*, *Fusarium graminearum*, *F. avenaceum*, *F. culmorum*, *Microdochium nivale*, *Puccinia striiformis*, *P. graminis*, *P. recondita*, *Micronectriella nivale*, *Typhula* sp., *Ustilago tritici*, *Tilletia caries*, *Pseudocercosporella herpotrichoides*, *Mycosphaerella graminicola*, *Stagonospora nodorum*, *Pyrenophora tritici-repentis*;

Barley diseases: *Erysiphe graminis*, *Fusarium graminearum*, *F. avenaceum*, *F. culmorum*, *Microdochium nivale*, *Puccinia striiformis*, *P. graminis*, *P. hordei*, *Ustilago nuda*, *Rhynchosporium secalis*, *Pyrenophora teres*, *Cochliobolus sativus*, *Pyrenophora graminea*, *Rhizoctonia solani*;

Maize diseases: *Ustilago maydis*, *Cochliobolus heterostrophus*, *Gloeocercospora sorghi*, *Puccinia polysora*, *Cercospora zeae-maydis*, *Rhizoctonia solani*;

Citrus diseases: *Diaporthe citri*, *Elsinoe fawcetti*, *Penicillium digitatum*, *P. italicum*, *Phytophthora parasitica*, *Phytophthora citrophthora*;

Apple diseases: *Monilinia mali*, *Valsa ceratosperma*, *Podosphaera leucotricha*, *Alternaria alternata* apple pathotype, *Venturia inaequalis*, *Colletotrichum acutatum*, *Phytophtora cactorum*;

Pear diseases: *Venturia nashicola*, *V. pirina*, *Alternaria alternata* Japanese pear pathotype, *Gymnosporangium haraeanum*, *Phytophtora cactorum*;

Peach diseases: *Monilinia fructicola*, *Cladosporium carpophilum*, *Phomopsis* sp.;

Grape diseases: *Elsinoe ampelina*, *Glomerella cingulata*, *Uninula necator*, *Phakopsora ampelopsidis*, *Guignardia bidwellii*, *Plasmopara viticola*;

Persimmon diseases: *Gloesporium kaki, Cercospora kaki, Mycosphaerela nawae;*

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans;*

Eggplant diseases: *Phomopsis vexans, Erysiphe cichoracearum;*

Brassicaceous vegetable diseases: *Alternaria japonica, Cercosporella brassicae, Plasmodiophora brassicae, Peronospora parasitica;*

Welsh onion diseases: *Puccinia allii, Peronospora destructor;*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora casiicola, Sclerotinia sclerotiorum;*

Kidney bean diseases: *Colletrichum lindemthianum;*

Peanut diseases: *Cercospora personata, Cercospora arachidicola, Sclerotium rolfsii;*

Pea diseases: *Erysiphe pisi;*

Potato diseases: *Alternaria solani, Phytophthora infestans, Phytophthora erythroseptica, Spongospora subterranean,* f. sp. Subterranean;

Strawberry diseases: *Sphaerotheca humuli, Glomerella cingulata;*

Tea diseases: *Exobasidium reticulatum, Elsinoe leucospila, Pestalotiopsis* sp., *Colletotrichum theae-sinensis;*

Tobacco diseases: *Alternaria longipes, Erysiphe cichoracearum, Colletotrichum tabacum, Peronospora tabacina, Phytophthora nicotianae;*

Rapeseed diseases: *Sclerotinia sclerotiorum, Rhizoctonia solani;*

Cotton diseases: *Rhizoctonia solani;*

Beet diseases: *Cercospora beticola, Thanatephorus cucumeris, Thanatephorus cucumeris, Aphanomyces cochlioides;*

Rose diseases: *Diplocarpon rosae, Sphaerotheca pannosa, Peronospora sparsa;*

Diseases of chrysanthemum andasteraceae: *Bremia lactuca, Septoria chrysanthemiindici, Puccinia horiana;*

Diseases of various plants: *Pythium aphanidermatum, Pythium debarianum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homeocarpa, Rhizoctonia solani;*

Banana diseases: *Mycosphaerella fijiensis, Mycosphaerella musicola;*

Sunflower diseases: *Plasmopara halstedii;*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymixa* spp., *Olpidium* spp. or the like.

Examples of the plants for which the "composition" can be used are as follows:

Agricultural crops: maize, rice, wheat, barley, rye, oat, sorghum, cotton, soybean, peanut, buckwheat, sugar beet, rapeseed, sunflower, sugar cane, tobacco, and the like;

Vegetables: Solanaceous vegetables (eggplant, tomato, green pepper, hot pepper, potato, etc.), Cucurbitaceous vegetables (cucumber, pumpkin, zucchini, watermelon, melon, squash, etc.); Cruciferous vegetables (radish, turnip, horseradish, kohlrabi, Chinese cabbage, cabbage, brown mustard, broccoli, cauliflower, etc.), Asteraceous vegetables (burdock, garland chrysanthemum, artichoke, lettuce, etc.), Liliaceous vegetables (Welsh onion, onion, garlic, asparagus, etc.), Umbelliferous vegetables (carrot, parsley, celery, parsnip, etc.), Chenopodiaceous vegetables (spinach, chard, etc.), Lamiaceous vegetables (Japanese basil, mint, basil, etc.), strawberry, sweet potato, yam, aroid, and the like;

Flowering plants;

Ornamental foliage plants;

Turf;

Fruit trees: pome fruits (apple, common pear, Japanese pear, Chinese quince, quince, etc.), stone fruits (peach, plum, nectarine, Japanese plum, cherry, apricot, prune, etc.), citrus (mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, and the like;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), and the like.

The above-described plants may be those having resistance imparted by genetic engineering technique.

Among the above plants, the "composition" is expected to have excellent controlling effect particularly to plant disease caused in soybean.

Among the above plant diseases, soybean diseases to which especially excellent effect of the "composition" can be expected are *Rhizoctonia solani, Cercospora kikuchii, Septoria glycines, Corynespora casiicola, Phakopsora pachyrizi, Sclerotinia sclerotiorum, Cercospora sojina,* and the like.

Following compositions exemplify an embodiment of the "composition":

a composition comprising "carboxamide compound (1)" and fipronil;

a composition comprising "carboxamide compound (1)" and ethiprole;

a composition comprising "carboxamide compound (2)" and fipronil;

a composition comprising "carboxamide compound (2)" and ethiprole;

a composition comprising "carboxamide compound (3)" and fipronil;

a composition comprising "carboxamide compound (3)" and ethiprole;

a composition comprising "carboxamide compound (4)" and fipronil;

a composition comprising "carboxamide compound (4)" and ethiprole;

a composition comprising "carboxamide compound (5)" and fipronil;

a composition comprising "carboxamide compound (5)" and ethiprole;

a composition comprising "carboxamide compound (1)" and fipronil in which the weight ratio of "carboxamide compound (1)" to fipronil is 0.01/1 to 4/1;

a composition comprising "carboxamide compound (1)" and ethiprole in which the weight ratio of "carboxamide compound (1)" to ethiprole is 0.01/1 to 4/1;

a composition comprising "carboxamide compound (2)" and fipronil in which the weight ratio of "carboxamide compound (2)" to fipronil is 0.01/1 to 4/1;

a composition comprising "carboxamide compound (2)" and ethiprole in which the weight ratio of "carboxamide compound (2)" to ethiprole is 0.01/1 to 4/1;

a composition comprising "carboxamide compound (3)" and fipronil in which the weight ratio of "carboxamide compound (3)" to fipronil is 0.01/1 to 4/1;

a composition comprising "carboxamide compound (3)" and ethiprole in which the weight ratio of "carboxamide compound (3)" to ethiprole is 0.01/1 to 4/1;

a composition comprising "carboxamide compound (4)" and fipronil in which the weight ratio of "carboxamide compound (4)" to fipronil is 0.01/1 to 4/1;

a composition comprising "carboxamide compound (4)" and ethiprole in which the weight ratio of "carboxamide compound (4)" to ethiprole is 0.01/1 to 4/1;

a composition comprising "carboxamide compound (5)" and fipronil in which the weight ratio of "carboxamide compound (5)" to fipronil is 0.01/1 to 4/1;

a composition comprising "carboxamide compound (5)" and ethiprole in which the weight ratio of "carboxamide compound (5)" to ethiprole is 0.01/1 to 4/1;

The method of controlling pest (hereinafter referred to as "controlling method") can be carried out by treating a plant or the soil where a plant grows with an effective amount of a "carboxamide compound" and "phenylpyrazole compound(s)".

The part of plant to be treated is stem and leaf of a plant, seed or bulb of a plant, and the bulb means bulb, corm, rootstock, tuber, tuberous root and rhizophore.

In the "controlling method", the treatment of a plant or the soil where a plant grows with a "carboxamide compound" and "phenylpyrazole compound(s)" can be carried out separately at the same timing, but the treatment is usually carried out by using a "composition" in light of convenience.

In the "controlling method", the treatment with a carboxamide compound" and "phenylpyrazole compound(s)" is, for example, stems and leaves application, soil application, roots application or seeds application.

Examples of the stems and leaves application include a treatment for surface of cultivated plant by a stem and leaves spray or a stem and tree spray.

Examples of the root application include a method of dipping a whole plant or the root of a plant into a liquid containing a "carboxamide compound" and "phenylpyrazole compound(s)" and a method of sticking a solid preparation comprising a "carboxamide compound", "phenylpyrazole compound(s)" and a solid carrier onto the root of a plant.

Examples of the soil application include a method of spraying a "composition" onto a soil, a method of mixing a "composition" with a soil and a method of irrigating a "composition" into the soil.

Examples of the seed application include a method of treating seeds or bulbs of a plant to be protected from a plant disease with a "composition". Particularly, the application can be carried out by spraying a suspension of a "composition" to the surface of seeds or bulbs, or by spreading wettable powder, emulsifiable concentrate or flowable formulation itself or a mixture thereof with a small amount of water on the seeds or the bulbs, or by dipping the seeds into a solution of a "composition" for a prescribed time, by film coating application or pellet coating application.

The amount of a "carboxamide compound" and "phenylpyrazole compound(s)" used in the "controlling method" is different depending on the kind of a plant to be treated, the kind of a plant disease to be controlled and its frequency, the kind of a formulation, timing of treatment, method of treatment, place of treatment, weather condition, and the like.

When a "composition" is applied to stems and/or leaves of a plant or to the soil where a plant grows, the total amount of a "carboxamide compound" and "phenylpyrazole compound(s)" is usually from 1 g to 500 g/1000 m$^2$, preferably from 2 g to 200 g/1000 m$^2$ and more preferably from 10 g to 100 g/1000 m$^2$.

When a "composition" is applied to seeds of a plant, the total amount of a "carboxamide compound" and "phenylpyrazole compound(s)" is usually from 0.001 g to 10 g/1 kg of the seeds, and preferably from 0.01 g to 1 g/1 kg of the seeds.

An emulsifiable concentrate, wettable powder or flowable formulation is usually used by diluting the formulation with a small amount of water and spraying the diluted formulation. In this case, the concentration of a "carboxamide compound" and "phenylpyrazole compound(s)" in total of the diluted formulation is usually from 0.0005% to 2% by weight and preferably from 0.005% to 1% by weight.

A powder formulation or granule formulation and the like is usually used without dilution.

EXAMPLE

The present invention is further explained in detail with Formulation Examples and Test Examples. However, the present invention is not limited by the following Examples.

In the following Examples, "part" means "part by weight" unless otherwise provided.

Formulation Example 1

One of the "carboxamide compound" (1) to (5) (2.5 parts), fipronil (1.25 parts), polyoxyethylene styryl phenyl ether (14 parts), calcium dodecylbenzene sulfonate (6 parts) and xylene (76.25 parts) are thoroughly mixed to give each of formulations, respectively.

Formulation Example 2

One of the "carboxamide compound" (1) to (5) (2 parts), fipronil (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 3

One of the "carboxamide compound" (1) to (5) (5 parts), fipronil (10 parts), sorbitan trioleate (1.5 parts), and an aqueous solution (28.5 parts) containing polyvinyl alcohol (2 parts) are mixed and the mixture is milled by wet-milling method. An aqueous solution (45 parts) containing xanthan gum (0.05 part) and aluminum magnesium silicate (0.1 part) is added to the milled mixture. To the mixture is added propylene glycol (10 parts) and the resultant mixture is mixed by stirring to give each of formulations, respectively.

Formulation Example 4

One of the "carboxamide compound" (1) to (5) (1 part), fipronil (4 parts), synthesized hydrous silicon oxide (1 part), calcium lignin sulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 5

One of the "carboxamide compound" (1) to (5) (12.5 parts), fipronil (37.5 parts), calcium lignin sulfonate (3 parts), sodium lauryl sulfate (2 parts) and synthesized hydrous silicon oxide (45 parts) are thoroughly mixed and milled to give each of formulations, respectively.

Formulation Example 6

One of the "carboxamide compound" (1) to (5) (3 parts), fipronil (2 parts), kaolin clay (85 parts) and talc (10 parts) are thoroughly mixed and milled to give each of formulations, respectively.

Formulation Example 7

One of the "carboxamide compound" (1) to (5) (2.5 parts), ethiprole (1.25 parts), polyoxyethylene styryl phenyl ether (14 parts), calcium dodecylbenzene sulfonate (6 parts) and xylene (76.25 parts) are thoroughly mixed to give each of formulations, respectively.

Formulation Example 8

One of the "carboxamide compound" (1) to (5) (2 parts), ethiprole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 9

One of the "carboxamide compound" (1) to (5) (5 parts), ethiprole (10 parts), sorbitan trioleate (1.5 parts), and an aqueous solution (28.5 parts) containing polyvinyl alcohol (2 parts) are mixed and the mixture is milled by wet-milling method. An aqueous solution (45 parts) containing xanthan gum (0.05 part) and aluminum magnesium silicate (0.1 part) is added to the milled mixture. To the mixture is added propylene glycol (10 parts) and the resultant mixture is mixed by stirring to give each of formulations, respectively.

Formulation Example 10

One of the "carboxamide compound" (1) to (5) (1 part), ethiprole (4 parts), synthesized hydrous silicon oxide (1 part), calcium lignin sulfonate (3 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 11

One of the "carboxamide compound" (1) to (5) (12.5 parts), ethiprole (37.5 parts), calcium lignin sulfonate (3 parts), sodium lauryl sulfate (2 parts) and synthesized hydrous silicon oxide (45 parts) are thoroughly mixed and milled to give each of formulations, respectively.

Formulation Example 12

One of the "carboxamide compound" (1) to (5) (3 parts), ethiprole (2 parts), kaolin clay (85 parts) and talc (10 parts) are thoroughly mixed and milled to give each of formulations, respectively.

Test Examples using each of the "compositions" are shown in the following.

Test Example

A cyclohexanone solution (100 microL) containing prescribed amount (weight) of a test compound was applied on seeds of soybean (variety: Natto shoryu) (10 g) by using a rotary apparatus for seed treatment (Seed dresser, manufactured by Hans-Ulrich Hege GmbH).

One day after the treatment, plastic pot was filled with soil contaminated by *Rhizoctonia solani*, and the seeds treated with the test compounds were seeded in the soil and cultivated in a glass-greenhouse for 20 days (hereinafter referred to as "treated plot").

Thereafter, the presence of disease caused by *Rhizoctonia solani* in the young plants which germinated from each seed was observed and disease severity was calculated according to the following calculation formula (1).

On the other hand, seeds of soybean which were not treated as above were cultivated in the same way as above (hereinafter referred to as "non-treated plot") and the disease severity in "non-treated plot" was calculated in the same way as above "treated plot". On the basis of the above disease severity in "treated plot" and the "non-treated plot", efficacy in "treated plot" was evaluated according to the following calculation formula (2).

The results are shown in Table 1 and Table 2.

Disease severity(%)=(number of infected young plants/total number of young plants)×100   Calculation formula (1)

Efficacy(%)=[1−(disease severity in "treated plot"/ disease severity in "non-treated plot")]×100   Calculation formula (2)

TABLE 1

| "carboxamide compound (1)" [g/100 kg of seeds] | fipronil [g/100 kg of seeds] | efficacy (%) |
|---|---|---|
| 0.2 | 5 | 68.4 |
| 0.2 | — | 42.1 |

TABLE 2

| "carboxamide compound (5)" [g/100 kg of seeds] | fipronil [g/100 kg of seeds] | efficacy (%) |
|---|---|---|
| 0.2 | 5 | 52.6 |
| 0.2 | — | 21.1 |

INDUSTRIAL APPLICABILITY

A pesticidal composition comprising a "carboxamide compound" represented by formula (I) and one or more phenylpyrazole compounds selected from group (A) is useful for controlling pests.

The invention claimed is:

1. A pesticidal composition comprising a carboxamide compound represented by formula (I):

[Chem. 1]

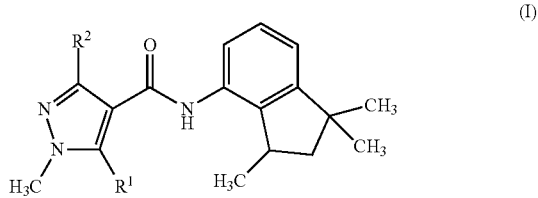

(I)

wherein $R^1$ represents a hydrogen atom or a methyl group, and $R^2$ represents a methyl group, a difluoromethyl group or a trifluoromethyl group, and one or more phenylpyrazole compounds selected from group (A) consisting of fipronil and ethiprole; wherein the weight ratio of the carboxamide compound to the phenylpyrazole compound(s) is from 0.01/1 to 4/1 of the carboxamide compound/the phenylpyrazole compound(s).

2. The pesticidal composition according to claim 1, wherein the phenylpyrazole compound is fipronil.

3. A method of controlling pest comprising a step of treating a plant or the soil where a plant grows with an effective amount of a carboxamide compound represented by formula (I):

[Chem. 2]

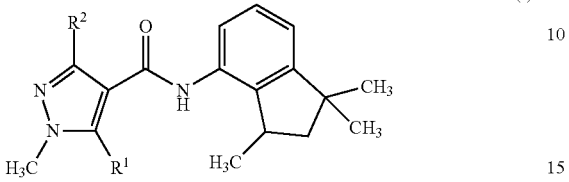

(I)

wherein $R^1$ represents a hydrogen atom or a methyl group, and $R^2$ represents a methyl group, a difluoromethyl group or a trifluoromethyl group, and one or more phenylpyrazole compounds selected from group (A) consisting of fipronil and ethiprole; wherein the weight ratio of the carboxamide compound to the phenylpyrazole compound(s) is from 0.01/1 to 4/1 of the carboxamide compound/the phenylpyrazole compound(s).

4. The method of controlling pest according to claim 3, wherein the phenylpyrazole compound is fipronil.

5. The method of controlling pest according to claim 3, wherein the plant or the soil where a plant grows is soybean or the soil where soybean grows, respectively.

\* \* \* \* \*